(12) United States Patent
Nurse et al.

(10) Patent No.: US 8,717,851 B1
(45) Date of Patent: May 6, 2014

(54) ALERT ANNOUNCER WITH REMOTE UNIT

(76) Inventors: Lloyd Cleveland Nurse, Decatur, GA (US); Darien Okinza Nurse, Decatur, GA (US)

(*) Notice: Subject to any disclaimer, the term of this patent is extended or adjusted under 35 U.S.C. 154(b) by 523 days.

(21) Appl. No.: 12/960,800

(22) Filed: Dec. 6, 2010

Related U.S. Application Data

(60) Provisional application No. 61/283,601, filed on Dec. 7, 2009.

(51) Int. Cl.
*G04C 21/16* (2006.01)

(52) U.S. Cl.
USPC .......................................... 368/10; 368/244

(58) Field of Classification Search
USPC ................. 368/10–11, 47, 244–245
See application file for complete search history.

(56) References Cited

U.S. PATENT DOCUMENTS

| | | | |
|---|---|---|---|
| 4,001,805 A | 1/1977 | Golbe | |
| 4,039,957 A | 8/1977 | Jennings | |
| 4,490,711 A | 12/1984 | Johnston | |
| 4,630,248 A | 12/1986 | Scott | |
| 5,012,223 A | 4/1991 | Griebell et al. | |
| 5,408,443 A | 4/1995 | Weinberger | |
| 6,717,598 B1* | 4/2004 | Melton et al. | 715/846 |
| 7,158,011 B2* | 1/2007 | Brue | 340/309.16 |
| 7,382,231 B2* | 6/2008 | Blumberg | 340/309.16 |
| 7,454,257 B2* | 11/2008 | McPherson et al. | 700/94 |
| 7,542,379 B2 | 6/2009 | Kimel et al. | |
| 7,545,257 B2 | 6/2009 | Brue | |
| 2004/0155780 A1* | 8/2004 | Rapchak | 340/573.1 |
| 2006/0017559 A1* | 1/2006 | Albert | 340/531 |
| 2006/0139150 A1* | 6/2006 | Brue | 340/309.16 |
| 2006/0215495 A1* | 9/2006 | Soled et al. | 368/10 |
| 2006/0280035 A1* | 12/2006 | Walker et al. | 368/10 |
| 2006/0285441 A1* | 12/2006 | Walker et al. | 368/10 |
| 2008/0068159 A1 | 3/2008 | Bradus et al. | |

(Continued)

FOREIGN PATENT DOCUMENTS

| WO | 2010132503 A | 11/2010 |
|---|---|---|
| WO | WO2010/013503 | 11/2010 |

OTHER PUBLICATIONS

Office Action issued on Aug. 27, 2013, U.S. Appl. No. 13/168,324.

*Primary Examiner* — Sean Kayes
(74) *Attorney, Agent, or Firm* — LeonardPatel PC; Michael A. Leonard, II; Sheetal S. Patel

(57) ABSTRACT

Disclosed are embodiments of an alert announcer system with and without a remote unit which alerts a person at medicine dosing times. The system comprises a primary unit; one or more medication modules, wherein each medication module has a plurality of medicine compartments; one alert device is attached to each medicine container monitored by the system; and optionally a remote unit. Medicine containers each have an alert device attached which executes a dosing schedule appropriate to the medicine in the container and produces an alert at medicine dosing times according to each individual dosing schedule. Medicine containers with attached alert devices are placed in or on the medication modules in predetermined physical locations. Medication modules detect alerts pertaining to each medicine container and transmit those alerts to the primary unit where an amplified sensible alert is generated to alert the user that it is time to take a dose of medicine. The primary unit may relay alerts to remote units or send notification via phone, text, mail or any other electronic means of communication.

12 Claims, 8 Drawing Sheets

(56) References Cited

U.S. PATENT DOCUMENTS

| | | |
|---|---|---|
| 2008/0074951 A1 | 3/2008 | Hubicki |
| 2008/0080319 A1 | 4/2008 | Niemiec et al. |
| 2008/0151695 A1 * | 6/2008 | Kimel et al. ............... 368/10 |
| 2009/0109800 A1 | 4/2009 | Kimel et al. |
| 2009/0281835 A1 | 11/2009 | Patwardhan et al. |
| 2010/0220553 A1 | 9/2010 | Nurse et al. |

* cited by examiner

ALERT ANNOUNCER WITH REMOTE UNIT

CROSS REFERENCE TO RELATED APPLICATIONS

This non-provisional application claims the benefit of prior filed provisional Application No. U.S. 61/283,601 entitled "Alert Announcer with Remote Unit" filed Dec. 7, 2009. Application No. U.S. 61/283,601 is incorporated herein by reference.

U.S. application Ser. No. 12/466,332 entitled "Method and Apparatus for Alerting a Person at Medicine Dosing Times" filed May 4, 2009 by the same inventors discloses embodiments of alert devices that may be used as components of the various system embodiments disclosed in the present application. U.S. application Ser. No. 12/466,332 is incorporated herein by reference.

STATEMENT REGARDING FEDERALLY SPONSORED RESEARCH OR DEVELOPMENT

Not Applicable.

DESCRIPTION OF ATTACHED APPENDIX

Not Applicable.

BACKGROUND

The present disclosure relates to the field of medicine. Medications are an important component of modern medical treatment. Medications are most effective and safest when taken in accordance with recommended dosing schedules. When medications are not taken in accordance with recommended dosing schedules they may become ineffective or even dangerous for the patient. The present disclosure provides systems and methods for addressing the need for improved patient compliance in taking medications according to recommended dosing schedules.

SUMMARY

The present disclosure is directed to alert announcer systems and methods which alert a person or persons at medicine dosing times. The systems disclosed provide monitoring of a plurality of medicine dosing schedules on a per medicine basis and also provide for alerts to be issued when one or more doses of medicine are to be taken.

An embodiment of an alert announcer system for alerting a person at medicine dosing times comprises: a primary unit comprising: a means for generating a first sensible alert; a first module transmitting channel; a means for receiving a module alert signal over the first module transmitting channel, the first sensible alert being generated in response to receiving the first module alert signal; a user responsive means for selectively altering the intensity of the first sensible alert; and, a user responsive means for recording, storing, and forwarding tag data associated with the module alert signal wherein the tag data is forwarded to the first means for generating a sensible alert when the module alert signal is received. This embodiment also comprises a medication module comprising: a plurality of medicine compartments, wherein each medicine compartment comprises a means for detecting a second sensible alert emitted by an alert device in proximity to that medicine compartment; the medication module transmitting the first module alert signal to the primary unit over the first module transmitting channel in response to detecting the second sensible alert; the first module alert signal comprising data indicating that the medication module detected at least one second sensible alert. In this embodiment the alert device comprises: an electronic timing device executing a dosing schedule appropriate for a medicine; and, a means for generating the second sensible alert, wherein the second sensible alert is generated at medicine dosing times according to the dosing schedule.

Another embodiment of an alert announcer system for alerting a person at medicine dosing times comprises: a primary unit comprising: a means for generating a first sensible alert; a first module transmitting channel; a means for receiving a first module alert signal over the first module transmitting channel, the first sensible alert being generated in response to receiving the first module alert signal; a user responsive means for selectively altering the intensity of the first sensible alert; and, a user responsive means for recording, storing, and forwarding tag data associated with the module alert signal wherein the tag data is forwarded to the first means for generating a sensible alert when the module alert signal is received. This embodiment also comprises: a medication module comprising: a plurality of medicine compartments, each medicine compartment comprising a means to detect a medication alert signal emitted by an alert device in proximity to that medicine compartment; the medication module transmitting said first module alert signal to the primary unit over the first module transmitting channel in response to receiving the medication alert signal; the first module alert signal comprising data indicating that the medication module detected at least one said medicine alert signal. In this embodiment the alert device comprises: an electronic timing device executing a dosing schedule appropriate for a medicine; and, a means for generating the medication alert signal, wherein the medication alert signal is generated at medicine dosing times according to the dosing schedule.

Another embodiment of an alert announcer system for alerting a person at medicine dosing times comprises: a remote unit comprising: a means for receiving a remote alert signal; a means for generating a remote sensible alert, wherein the remote sensible alert is generated in response to receiving the remote alert signal; and, a remote user responsive means for selectively altering the intensity of the remote sensible alert. This embodiment also comprises a primary unit comprising: a means for transmitting the remote alert signal; a first module transmitting channel; a means for receiving a first module alert signal over the first module transmitting channel, the remote alert signal being transmitted in response to receiving the first module alert signal over the first module transmitting channel; a user responsive means for recording, storing, and forwarding tag data associated with the module alert signal wherein the tag data is included in the remote alert signal; a means for generating a sensible alert, the sensible alert being generated in response to receiving the first module alert signal; and, a user responsive means for selectively altering the intensity of the first sensible alert. This embodiment also comprises a medication module comprising: a plurality of medicine compartments, each medicine compartment comprising a means to detect a medication alert signal emitted by an alert device in proximity to that medicine compartment; the medication module transmitting the first module alert signal to the primary unit over the first module transmitting channel in response to receiving the medication alert signal; the first module alert signal comprising data indicating that the medication module detected at least one the medication alert signal. In this embodiment the alert device comprises: an electronic timing device executing a dosing schedule appropriate for a medicine; means for generating the medication alert signal, wherein the medicine alert signal is generated at medicine dosing times according to the dosing schedule.

Another embodiment of an alert announcer system for alerting a person at medicine dosing times comprises: a primary unit comprising: a means for generating a first sensible alert; a first module transmitting channel; a means for receiving a first module alert signal over the first module transmitting channel, the first sensible alert being generated in response to receiving the first module alert signal; a user responsive means for selectively altering the intensity of the first sensible alert; and, a user responsive means for recording, storing, and forwarding tag data associated with the module alert signal wherein the tag data is forwarded to the first means for generating a sensible alert when the module alert signal is received. This embodiment further comprises a medication module comprising: a plurality of medicine compartments, wherein each medicine compartment comprises: an electronic timing device executing a dosing schedule appropriate for a medicine; a means for generating a medication alert signal, the medication alert signal being generated at medicine dosing times according to the dosing schedule; a means for detecting a medication alert signal; and; a user responsive means for starting and stopping the execution of the dosing schedule. In this embodiment the medication module transmits the first module alert signal to the primary unit over the first module transmitting channel in response to receiving the medication alert signal, and the first module alert signal comprises data indicating that the medication module detected at least one the medicine alert signal.

BRIEF DESCRIPTION OF THE DRAWINGS

These and other features, aspects, and advantages of the present invention will become better understood with regard to the following description, appended claims, and accompanying drawings where:

LIST OF REFERENCE NUMBERS APPEARING IN THE FIGURES

Figure 1:
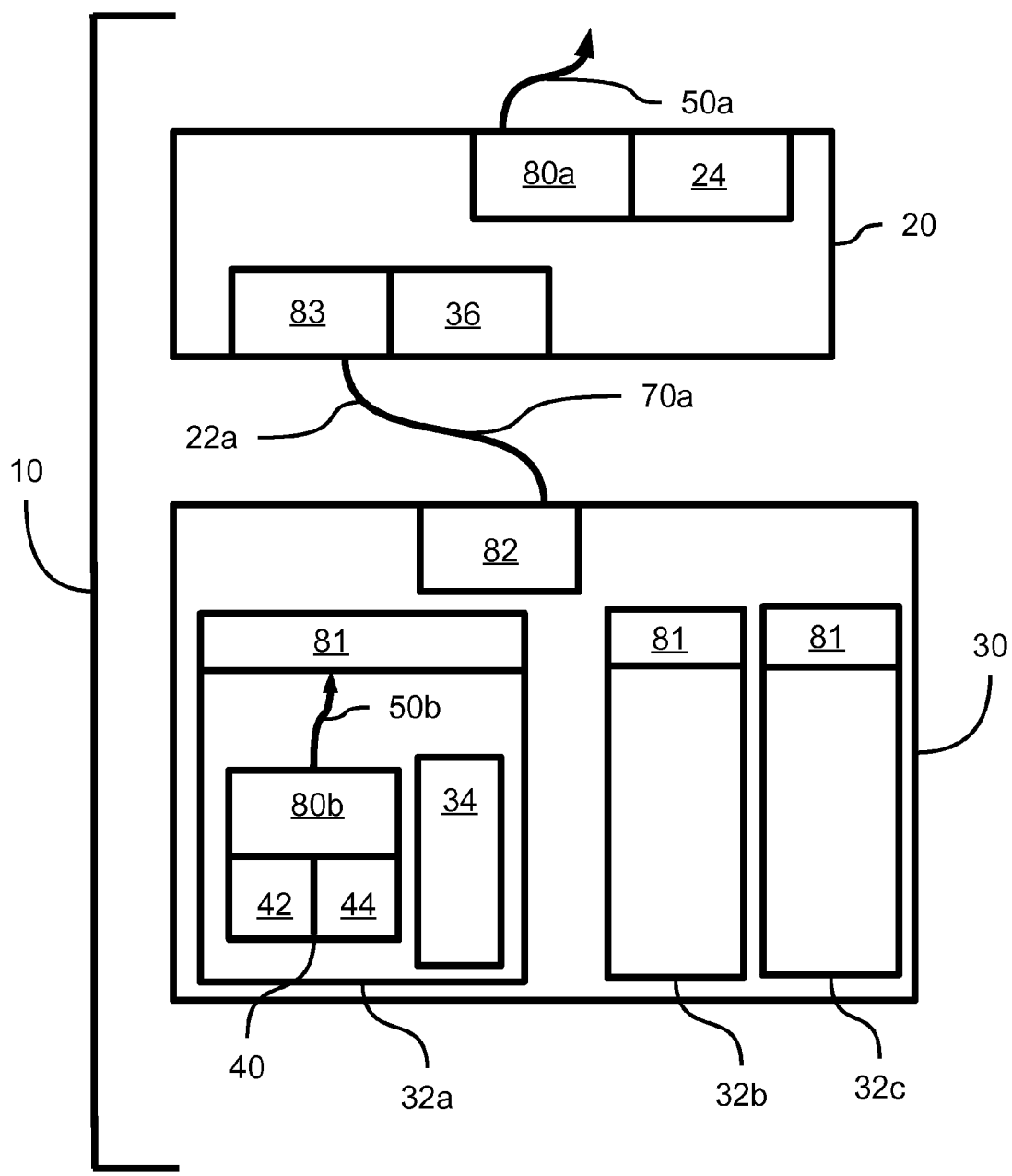
FIG. 1 shows a functional block diagram of an alert announcer system for alerting a person at medicine dosing times according to an embodiment of the present disclosure.

10—alert announcer system
20—primary unit
22, 22a, 22b—module transmitting channel, first module transmitting channel, second module transmitting channel
24—user responsive means for selectively altering the intensity of an alert
24r—remote user responsive means for selectively altering the intensity of an alert
26—remote unit
28—user responsive means for interacting with a device executing a dosing schedule
30, 30a, 30b—medication module, first medication module, second medication module
32, 32a, 32b, 32c—medicine compartment, first medicine compartment, second medicine compartment, third medicine compartment
34, 34a, 34b—medicine container, first medicine container, second medicine container
36—user responsive means for recording, storing, and forwarding tag data
36a, 36b—first and second user responsive means for recording, storing, and forwarding tag data
40, 40a, 40b—alert device, first alert device, second alert device etc.
42—electronic timing device
44, 44a, 44b—dosing schedule, first dosing schedule, second dosing schedule
50, 50a, 50b—sensible alert, first sensible alert, second sensible alert
50r—remote sensible alert
50b1, 50b2—second sensible alert 1, second sensible alert 2
60, 60a, 60b—medication alert signal, first medication alert signal, second medication alert signal
70, 70a, 70b—module alert signal, first module alert signal, second module alert signal
80—means for generating a sensible alert
80a, 80b—first and second means for generating a sensible alert
80r—remote means for generating a sensible alert
81—means for detecting a sensible alert
82—means for generating a module alert signal
83—means for detecting a module alert signal
84—means for generating a medication alert signal
85—means for detecting a medication alert signal
88—means for transmitting a remote alert signal
89—means for receiving a remote alert signal
90—remote alert signal

DESCRIPTION

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention can be practiced without these specific details. In other instances, well-known structures and devices are shown in block diagram form in order to facilitate describing the present invention.

Note that in this disclosure, references to "one embodiment" or "an embodiment" mean that the feature being referred to is included in at least one embodiment of the present disclosure. Furthermore, separate references to "one embodiment" or "an embodiment" in this disclosure do not necessarily refer to the same embodiment, however, such embodiments are not mutually exclusive unless so stated, and except as will be readily apparent to those skilled in the art from the description. For example, a feature, structure, act, etc. described in one embodiment may also be included in other embodiments. Thus the present invention can include a variety of combinations and/or integrations of the embodiments described herein.

The present disclosure describes various embodiments of an alert announcer system for alerting a person at medicine dosing times. The system is comprised of a number of components that act in coordination with each other to accomplish the goal of alerting a person at medicine dosing times. When the system or components of the system produce an alert that is intended to get the attention of a person that alert is referred to as a sensible alert. A sensible alert is an alert that can be sensed by a person. Preferred modalities of sensible alerts include visual, auditory, and tactile. In addition to generating sensible alerts the system or components of the system may produce alert signals. An alert signal should be understood to mean a signal that is communicated from one part of the system to another part of the system. Alert signals in various forms are used to communicate within the system and serve to indicate to the system that a sensible alert should be generated by the system.

Turning now to FIG. 1, shown is a functional block diagram of an alert announcer system 10 for alerting a person at medicine dosing times according to an embodiment of the present disclosure. The system of FIG. 1 is shown comprising: primary unit 20 comprising: a first means 80a for generating a first sensible alert 50a; a first module transmitting channel 22a; and, means 83 for receiving a module alert signal 70a over first module transmitting channel 22a. First sensible alert 50a is generated in response to receiving first module alert signal 70a. Primary unit 20 additionally comprises: user responsive means 24 for selectively altering the intensity of first alert 50a; and, user responsive means 36 for recording, storing, and forwarding tag data. Means 36 is user responsive and operates to record, store and forward tag data associated with first module alert signal 70a. By way of example, a user may record a voice tag, perhaps the name of a person, using means 36. Means 36 may store that voice tag and then forward that voice tag to means 80a when first module alert signal 70a is detected. Means 80a may be configured to replay the recorded voice tag when sensible alert 50a is generated. The type of tag data recorded, stored and forwarded by means 36 is not limited to voice data. Tag data may include text, blinking codes, tones, music, ring tones, and other modalities that are within the capability of means 80a to produce. Means 36 may also include means to reset tag data.

The system of FIG. 1 is shown further comprising: a medication module 30 comprising: a plurality of medicine compartments 32a, 32b, and 32c. Each medicine compartment comprises a predetermined physical area suitable for the placement of a medicine container 34. Each medicine compartment also comprises means 81 for detecting a second sensible alert 50b emitted by an alert device 40 in proximity to that medicine compartment. Medication module 30 transmits first module alert signal 70a to primary unit 20 over first module transmitting channel 22a in response to detecting second sensible alert 50b. Means 82 for generating module alert signal operates to generate first module alert signal 70a in response to medication module 30 detecting a sensible alert signal in any of the medication compartments 32a, 32b, and 32c. First module alert signal 70a comprises data indicating that a second sensible alert was detected from at least one medication compartment. First module alert signal 70a may additionally comprise data identifying which medicine compartment detected second sensible alert.

In preferred embodiments of the system shown in FIG. 1 alert device 40 will be attached to medicine container 34. Each medicine compartment has a size and orientation that facilitates the physical placement of the medicine container on, near, or within the physical space defined for each medicine compartment. Moreover, the plurality of medicine compartments are configured so that the means for detecting the sensible alert generated by the alert device will detect sensible alerts that are generated by the alert device that is substantially on, near, or within the confines of the physical space defined for that medicine compartment. Also, it must be pointed out that although FIG. 1 shows and embodiment of the system in which the medication module has three medication compartments, embodiments having more or fewer medication compartments are entirely within the spirit and scope of the present disclosure.

With continuing reference to FIG. 1, the system is shown further comprising alert device 40 which is shown as located substantially within the confines of the physical space defined for medicine compartment 32a. Alert device 40 is shown comprising: electronic timing device 42 which executes a dosing schedule 44 appropriate for the medication contained in medicine container 34. Alert device 40 additionally comprises means 80b for generating the second sensible alert 50b. Alert device 40 operates to generate second sensible alert 50b at medicine dosing times according to dosing schedule 44.

Sensible alerts may be visual, auditory, or tactile. A visual alert may be produced by lights, light emitting diodes (LEDs), or other suitable visual indicators as are known in the art. An auditory alert may be produced in the form of buzzer, bell, music, tone, synthesized voice, recorded voice, or other suitable auditory indicators as are known in the art. Tactile alerts may be produced by vibrating mechanisms or other suitable tactile indicators as are known in the art. Sensible alerts of visual, auditory, and tactile modes may be produced singly or in any combination and such combinations are within the spirit and scope of the present disclosure. In preferred embodiments the sensible alert produced by the primary unit may be more intense, brighter, and louder than the sensible alerts produced by individual alert devices. In preferred embodiments it may be the case that the alert devices are low power devices, whereas the primary unit may be operated at a higher power.

The intensity of a sensible alert may be made responsive to user adjustment by providing knobs, switches, sliders, or buttons which are operably connected to the means by which those sensible alerts are produced. Altering the power level and/or duty cycle used to drive the sensible alert generating means alters the intensity of the sensible alert produced. In addition, alerts may be reset and hushed by user responsive means to further control the system. These capabiltities, individually or in combination are enabled by user responsive means 24 for selectively altering the intensity of sensible alerts generated by primary unit 20.

Sensible alerts may be detected by module sensors according to their modality whether it be visual, auditory, or tactile, by light sensitive detector circuits, sound sensitive detector circuits, or by vibration sensitive detector circuits, respectively, as are known in the art.

Module alert signals may be generated, transmitted, and received by electrical, optical, or radio frequency means as are known in the art. Module transmitting channels may be constructed according to the type of module alert signals generated and may be electrical, or radio frequency in nature, with electrical preferred.

It is noted that the embodiment described in FIG. 1 makes clear that it is within the spirit and scope of the present disclosure that a medication module may comprise any practical number of individual medication compartments as long as: each compartment has a suitable and operative means 81 for detecting a sensible alert; each alert device 40 placed in or on the medication module must generate a sensible alert compatible with the means used to detect that alert. In some embodiments the module alert signal may additionally comprise data identifying which medicine compartment detected second sensible alert 50*b*.

With continuing reference to FIG. 1, preferred operation and use of the system would typically proceed as follows. The following description assumes that the primary unit 20 and medication module 30 have both been supplied with power sufficient for proper operation and that module transmitting channel 22*a* linking primary unit 20 and medication module 30 is operable. The user may choose to record and store tag data by using user responsive means 36 for recording, storing, and forwarding tag data. Then with a medication in a free standing medicine container 34, a person would select an alert device 40 that is programmed to execute a dosing schedule 44 appropriate for that medication. The alert device 40 may then be attached to medicine container 34. Alert device 40 may be caused by the user to start executing its dosing schedule 44 at the appropriate time as determined by the user, generally referred to in this system as the "Initial Start Time". The alert device-medicine container combination may then be placed in or on medication module 30 in an unoccupied medicine compartment 32*a*. When electronic timing device 42 arrives at a dosing time as indicated by dosing schedule 44, alert device 40 will produce second sensible alert 50*b* via second means 80*b* for generating a sensible alert. Means 81 for detecting a sensible alert that is associated with medicine compartment 32*a* will then detect second sensible alert 50*b*. The detection of the sensible alert is transformed by means 82 for generating a module alert signal which then transmits first module alert signal 70*a* over first module transmitting channel 22*a*. First module alert signal 70*a* contains data indicating that a device alert has been detected. In some embodiments module alert signal 70*s* may additionally comprise data indicating that a sensible alert was detected in relation to medicine compartment 32*a*. Then in primary unit 20 means 83 for detecting a module alert signal will detect module alert signal 70*a*. In response to detecting module alert signal 70*a* user responsive means 36 for recording, storing, and forwarding tag data operates to forward tag data along with the module alert signal to means 80*a*. Primary unit 20 will then generate first sensible alert 50*a* using first means 80*a* for generating a sensible alert. If the user has previously recorded tag data then that data would be forwarded to means 80*a* in response to the primary unit 20 receiving first module alert signal 70*a*. Upon sensing the sensible alert a person would then identify the medicine container that is in a state of alert and then take the appropriate medication. A person may then hush or reset alert device 40. A person may also interact with primary unit 20 via user responsive means 24 for selectively altering the intensity of an alert to hush the alert, reset the alert, turn off the alert, and/or change the volume or intensity of the alert as deemed appropriate by the user.

Preferred embodiments of alert device 40 used in the system of FIG. 1 are constructed according to embodiments of U.S. Application Ser. No. 12/466,332 entitled "Method and Apparatus for Alerting a Person at Medicine Dosing Times". In that application apparatuses are disclosed that suit the needs of alert device 40 shown in FIG. 1. An alert device according to that disclosure comprises an electronic timing mechanism that executes a medicine dosing schedule and alerts a person at times that correspond to the times at which doses of medicine should be administered. The alert device may be constructed using a flexible substrate upon which are mounted the electronic timing mechanism, one or more annunciators, and one or more switches. The flexible substrate is provided with a means of attaching the apparatus to other objects, and the flexibility of the apparatus is such that it can conform to curved surfaces of other objects. Thus the apparatus may be operable while substantially conforming to the medicine container to which it is attached.

Figure 2:
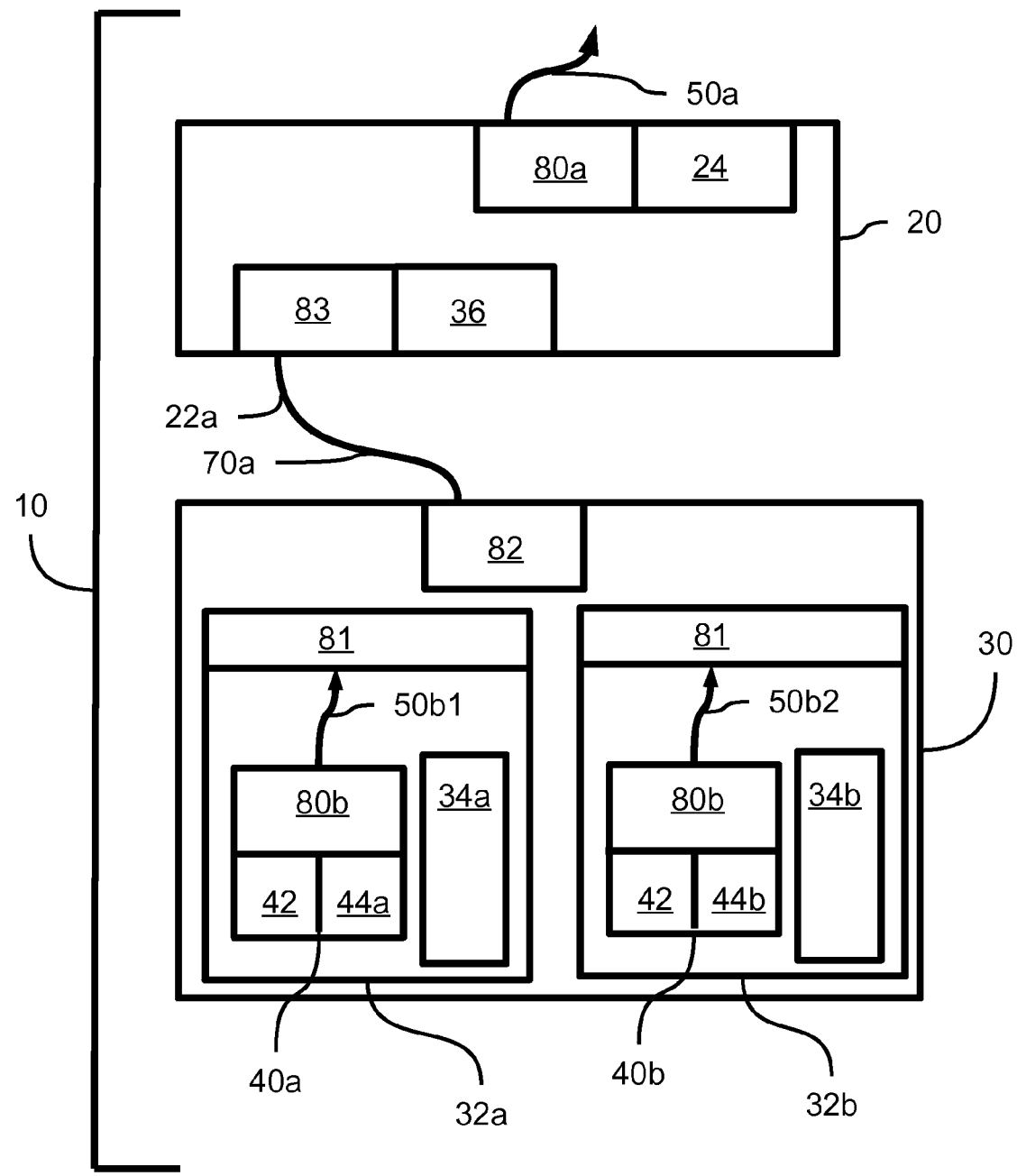
FIG. 2 shows a functional block diagram of an alert announcer system for alerting a person at medicine dosing times according to an embodiment of the present disclosure.

Turning now to FIG. 2, shown is a functional block diagram of the alert announcer system 10 of FIG. 1 with the addition of a second alert device 40*b* attached to a second medicine container 34*b* and the alert device-medicine container combination placed substantially in or on second medicine compartment 32*b*. Second alert device 40*b* executes second dosing schedule 44*b* which is appropriate for the medicine contained in medicine container 34*b*. Second medicine compartment 32*b* has means 81 for detecting a sensible alert. Alert device 40*b* operates to generate second sensible alert 50*b*2 at medicine dosing times according to dosing schedule 44*b*. When the means 81 for detecting a sensible alert that is associated with second medicine compartment 32*b* detects sensible alert 50*b*2, means 82 for generating module alert signal operates to generate first module alert signal 70*a* in response to medication module 30 detecting a sensible alert signal in any of the medication compartments 32*a*, 32*b*, and 32*c*. First module alert signal 70*a* comprises data indicating that a second sensible alert was detected from at least one medication compartment. First module alert signal 70*a* may additionally comprise data identifying which medicine compartment detected second sensible alert. Primary unit 20 and first module transmitting channel 22*a* of FIG. 2 operate in the same way as the same structures of FIG. 1 and those operations result in the generation of first sensible alert 50*a* which alerts a person that a dose of medicine from medicine container 34*b* should be taken. User responsive means 36 for recording, storing, and forwarding tag data may be used to associate tag data with the occurrence of module alert signal 70*a*. Tag data previously stored by means 36 may be forwarded to means 80*a* upon receipt of module alert signal by means 83.

Figure 3:
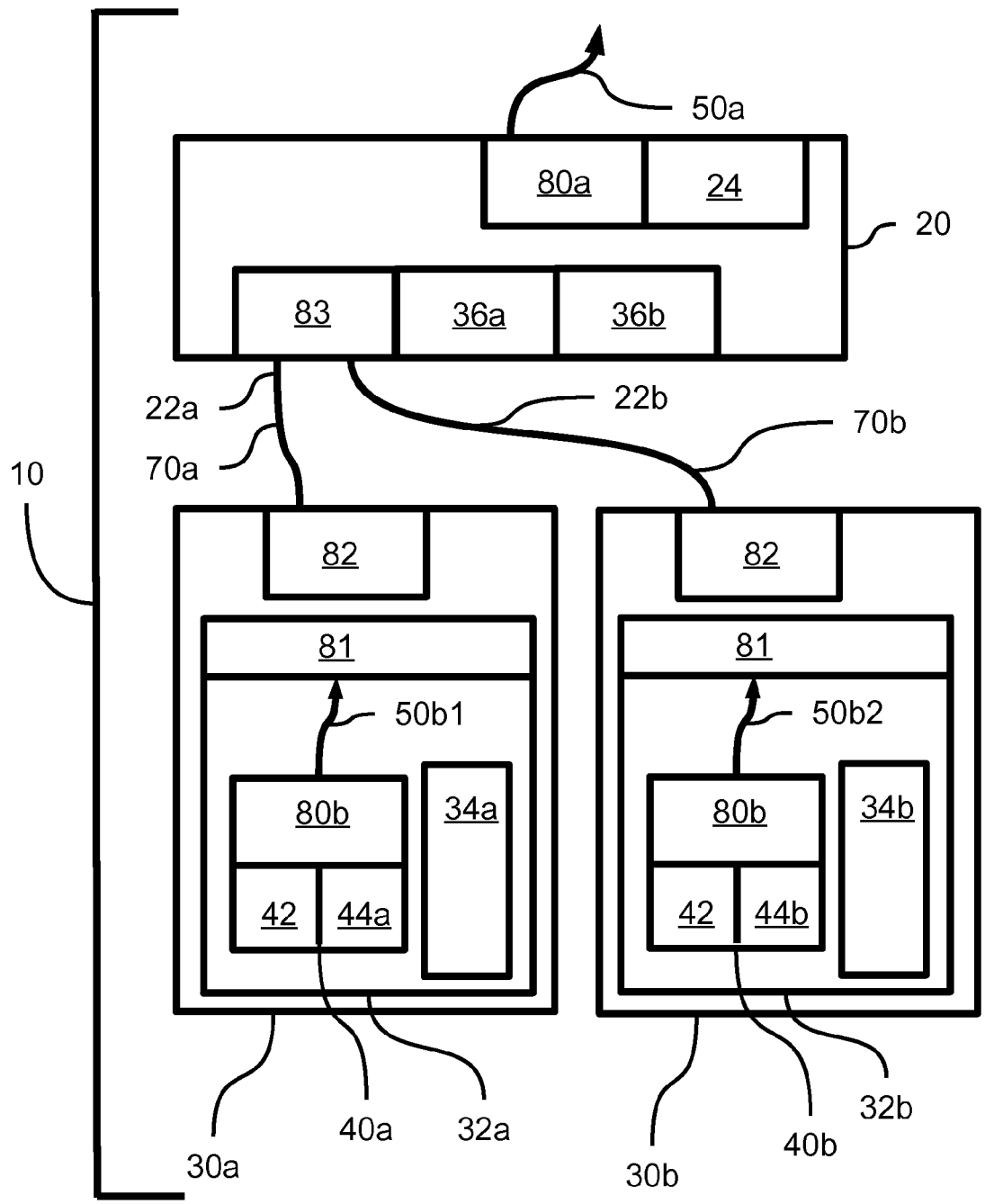
FIG. 3 shows a functional block diagram of an alert announcer system for alerting a person at medicine dosing times according to an embodiment of the present disclosure.

Turning now to FIG. 3, shown is a functional block diagram of an alert announcer system 10 for alerting a person at medicine dosing times according to an embodiment of the present disclosure. While the same in many respects to the systems of FIG. 1 and FIG. 2, the system of FIG. 3 has a few differences noted here. FIG. 3 is shown comprising both a first medication module 30*a* and a second medication module 30*b*. First medication module 30*a* comprises means 82 for generating a module alert signal and is operable to transmit first module alert signal 70*a* via first module transmitting channel 22*a* to primary unit 20. In like manner, second medication module 30*a* comprises means 82 for generating a module alert signal and is operable to transmit second module alert signal 70*b* via second module transmitting channel 22*b* to primary unit 20. Means 83 for detecting a module alert signal is adapted to support multiple module transmitting channels and is adapted to distinguish between alert signals generated by first medication module 30*a* and second medication module 30*b*. Module alert signals may comprise data indicating which module generated the module alert signal. First means 80*a* for generating a sensible alert are operative to produce first sensible alert 50*a* in response to primary unit 20 detecting either first module alert signal 70*a* or second module alert signal 70*b*. Primary unit 20 is shown comprising user responsive means 24 for selectively altering the intensity of an alert. User responsive means 24 for selectively altering the intensity of an alert may be configured so that sensible alerts caused by module alert signals received on different module transmitting channels are individually alterable.

With continuing reference to FIG. 3, primary unit 20 is shown additionally comprising: first means 36a for recording, storing, and forwarding tag data; and, second means 36b for recording, storing, and forwarding tag data. First means 36a is user responsive and operates to record, store and forward tag data associated with first module alert signal 70a. Second means 36b is user responsive and operates to record, store and forward tag data associated with second module alert signal 70b. By way of example, a user may record a voice tag, perhaps the name of a person, using means 36a. Means 36a may store that voice tag and then forward that voice tag to means 80a when first module alert signal 70a is detected. Means 80a may be configured to replay the recorded voice tag when sensible alert 50a is generated. Means 36b may operate in a similar fashion such that the user may record and store voice tag data associated with second module alert signal 70b may be different from the tag data associated with first module alert signal 70a. The type of tag data recorded, stored and forwarded by means 36a and 36b is not limited to voice data. Tag data may include text, blinking codes, tones, music, ring tones, and other modalities that are within the capability of means 80a to produce.

With continuing reference to FIG. 3, first module alert signal 70a comprises data indicating that a second sensible alert was detected from at least one medication compartment in medication module 30a. First module alert signal 70a may additionally comprise data identifying which medicine compartment detected second sensible alert. First module alert signal 70a may additionally comprise data identifying which medication module detected second sensible alert. In like manner, second module alert signal 70b comprises data indicating that a second sensible alert was detected from at least one medication compartment in medication module 30b. Second module alert signal 70b may additionally comprise data identifying which medicine compartment detected second sensible alert. Second module alert signal 70b may additionally comprise data identifying which medication module detected second sensible alert.

It is noted that the embodiment described in FIG. 3 makes clear that it is within the spirit and scope of the present disclosure to use any practical number of individual medication modules as long as: means 83 for detecting a module alert signal is adapted to support the number medication modules desired; additional module transmitting channels are added as needed; and, additional means for recording, storing, and forwarding tag data are added as needed to support the number of module alert signals used in the system.

Figure 4:
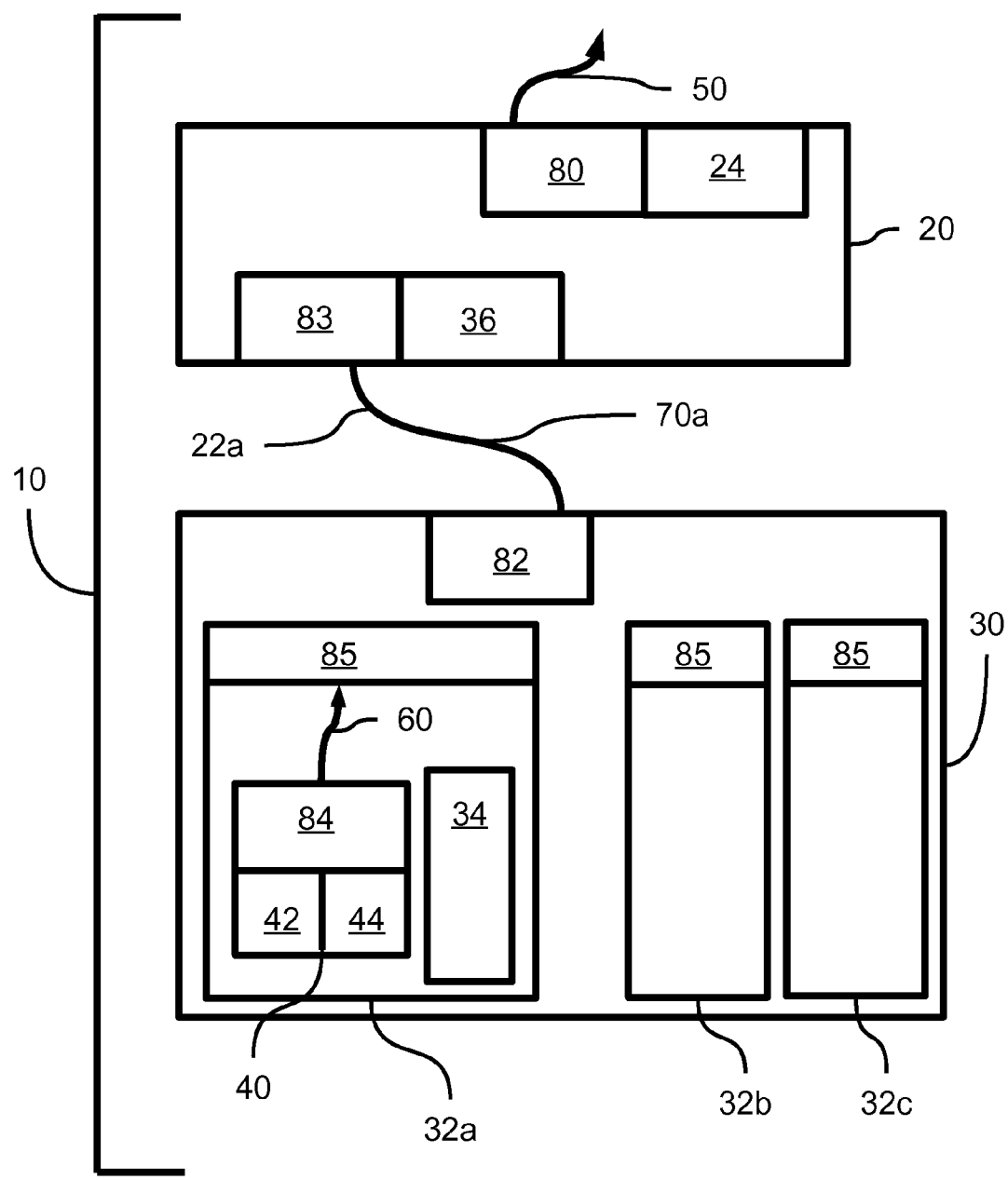
FIG. 4 shows a functional block diagram of an alert announcer system for alerting a person at medicine dosing times according to an embodiment of the present disclosure.

Turning now to FIG. 4, shown is a functional block diagram of an alert announcer system 10 for alerting a person at medicine dosing times according to an embodiment of the present disclosure. While the same in many respects to the system of FIG. 1, the system of FIG. 4 has a few differences noted here. In the system of FIG. 4 alert device 40 has means 84 for generating a medication alert signal which produces a medication alert signal 60 at medicine dosing times according to dosing schedule 44. Medication alert signal 60 may be electrical or optical and is not sensible to a person. Each medication compartment 32a, 32b, and 32c has a means 85 for detecting a medication alert signal. Means 82 for generating module alert signal operates to generate first module alert signal 70a in response to medication module 30 detecting a sensible alert signal in any of the medication compartments 32a, 32b, and 32c. First module alert signal 70a comprises data indicating that a medication alert signal was detected from at least one medication compartment. First module alert signal 70a may additionally comprise data identifying which medicine compartment detected a medication alert signal. Medication module 30 transmits first module alert signal 70a to primary unit 20 over first module transmitting channel 22a in response to detecting medication alert signal 60. In primary unit 20 means 83 for detecting a module alert signal detects module alert signal 70a. User responsive means 36 for recording, storing, and forwarding tag data operates the same as means 36 of FIG. 1 with the same features and advantages. If the user has previously recorded tag data then that data will be forwarded to means 80 as a result of means 83 detecting module alert signal 70a. In response to detecting module alert signal 70a primary unit 20 will then generate a sensible alert 50 using means 80 for generating a sensible alert.

Medication alert signals may be generated, transmitted, and received by electrical or optical means as are known in the art. Low power means for generating medication alert signals are preferred. By way of example, means 84 may be configured to emit a brief electrical pulse over a pair of conductors that is sensed by means 85. Means 85 may sense the emitted pulse by direct contact or by inductive, capacitive, or other non-contact sensing methods.

It is noted that the embodiment described in FIG. 4 makes clear that it is within the spirit and scope of the present disclosure that a medication module may comprise any practical number of individual medicine compartments as long as: each compartment has a suitable and operative means 85 for detecting a medication alert signal 60; each alert device 40 placed in or on the medication module 30 generates a medication alert signal 60 compatible with the means used to detect that medication alert signal; and, first module alert signal 70a comprises data indicating that a medication alert signal was detected from at least one medication compartment. First module alert signal 70a may additionally comprise data identifying which medicine compartment detected medication alert signal.

Figure 5:
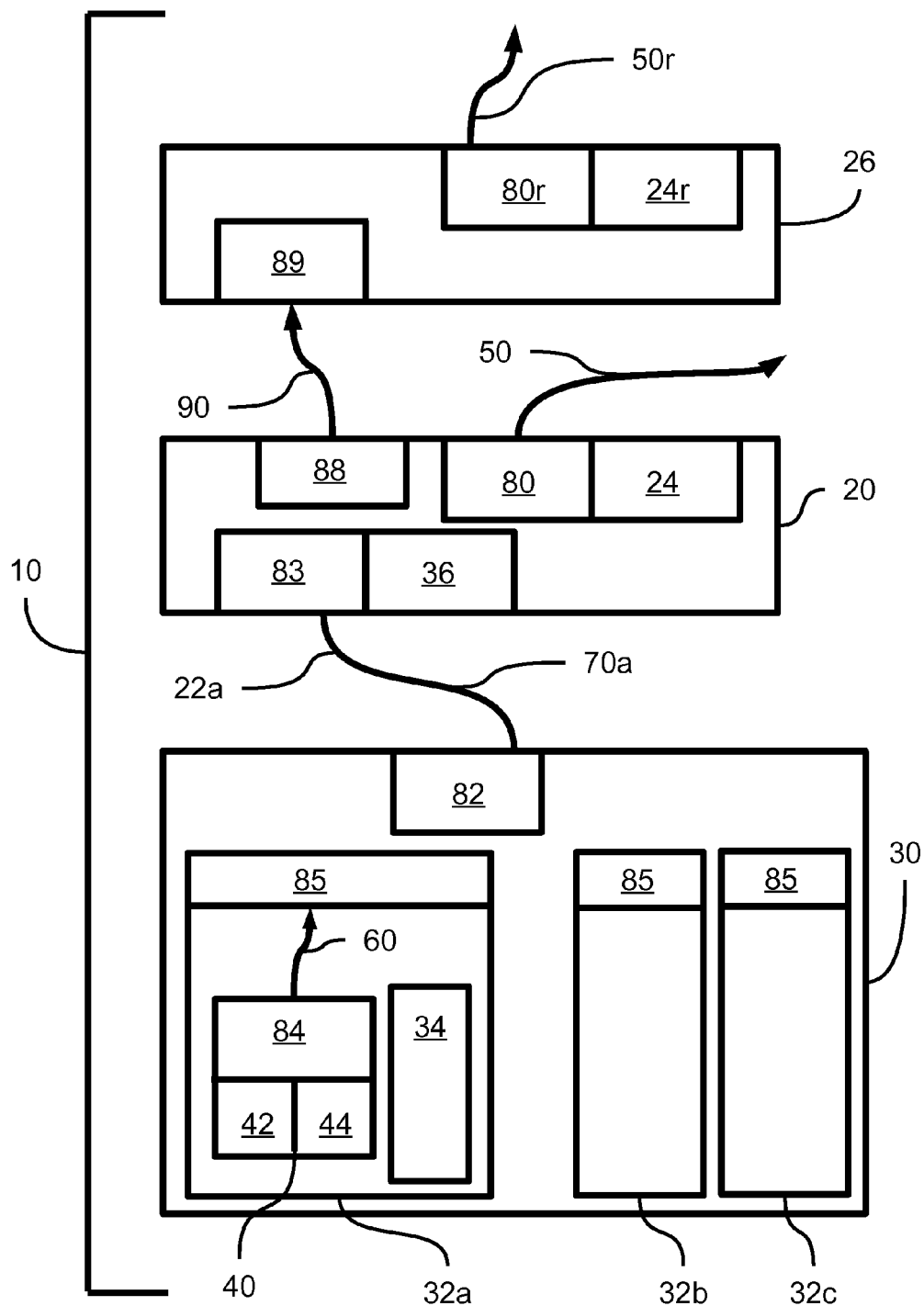
FIG. 5 shows a functional block diagram of an alert announcer system for alerting a person at medicine dosing times according to an embodiment of the present disclosure.

Turning now to FIG. 5, shown is a functional block diagram of an alert announcer system 10 for alerting a person at medicine dosing times according to an embodiment of the present disclosure. The system of FIG. 5 is shown comprising: a remote unit 26 which generates remote sensible alert 50r in response to receiving remote alert signal 90; primary unit 20 which transmits remote alert signal 90 in response to detecting first module alert signal 70a; and, medication module 30 which generates first module alert signal 70a in response to detecting a medication alert signal 60 from any one of a plurality of medicine compartments 32a, 32b, or 32c. Remote unit 26 is shown further comprising: remote means 80r for generating a sensible alert; a remote user responsive means 24r for selectively altering the intensity of an alert; and, means 89 for receiving a remote alert signal. Primary unit 20 is shown additionally comprising: means 88 for transmitting remote alert signal 90; means 83 for detecting a module alert signal via first module transmitting channel 22a; means 80 for generating a sensible alert which operates to generate sensible alert 50 in response to receiving first module alert signal 70a; means 24 for selectively altering the intensity of sensible alert 50; and, user responsive means 36 for recording, storing, and forwarding tag data. Means 36 is user responsive and operates to record, store and forward tag data associated with first module alert signal 70a. By way of example, a user may record a voice tag, perhaps the name of a person, using means 36. Means 36 may store that voice tag and then forward that tag data to means 88 when first module alert signal 70a is detected. Means 88 may be configured to transmit that voice tag data as part of remote alert signal 90. When received by means 89 that voice tag data may be forwarded to means 80r for use in alerting a person. Means 36 may also forward that voice tag data to means 80 for use in alerting a person. The type of tag data recorded, stored and forwarded by means 36 is not limited to voice data. Tag data may include text, blinking codes, tones, music, ringtones, and other modalities that are within the capability of means 80 or 80r to produce. Means 36 may also include means to reset tag data.

With continuing reference to FIG. 5, medication module 30 is shown comprising: means 82 for generating a module alert signal 70a; and a plurality of medicine compartments 32a, 32b, and 32c, wherein each medicine compartment comprises means 85 for detecting a medication alert signal 60 emitted by an alert device 40 in proximity to that medicine compartment.

With continuing reference to FIG. 5, alert device 40 is shown as located substantially within the confines of the physical space defined for medicine compartment 32a. Alert device 40 is shown comprising: electronic timing device 42 which executes a dosing schedule 44 appropriate for the medication contained in medicine container 34. Alert device 40 additionally comprises means 84 for generating the medication alert signal 60. Alert device 40 operates to generate medication alert signal 60 at medicine dosing times according to dosing schedule 44.

Remote unit 26 may be a purpose built device or it may be a general purpose device such as a cell phone that has been adapted for its application in the present system. Remote alert signal 90 may be electrical, optical, or radio frequency and may be transmitted and received by means 88 for transmitting a remote alert signal and means 89 for receiving a remote alert signal, respectively, by means known in the art. By way of example and not of limitation, means 88 for transmitting a remote alert signal may dial a phone, send an email, send a text message, send a page, or emit a radio frequency pulse or continuous carrier. In addition, remote alert signal 90 comprises: data indicating which medication module caused the generation of the remote alert signal. In some embodiments remote alert signal 90 may comprise data indicating which medicine compartment caused the production of the module alert signal. Remote sensible alert 50r may be generated by means 80r according its modality whether it be visual, auditory, or tactile, by light generating circuits, sound generating circuits, or by vibration generating circuits, respectively, as are known in the art. Remote user responsive means 24r for selectively altering the intensity of an alert operates in similar fashion to means 24 as shown and described in FIG. 1, FIG. 2, FIG. 3, and FIG. 4.

Remote unit 26 may be constructed to receive and distinguish between a plurality of remote alert signals transmitted by more than one primary units. By way of example and not of limitation, remote unit 26 may comprise means 89 for detecting remote alert signal that is operable to detect remote alert signals at a plurality of radio frequencies. A plurality of primary units could each use a different radio frequency when transmitting their remote alert signals. Thus a plurality of primary units may be monitored using one remote unit.

It is noted that the embodiment described in FIG. 5 makes clear that it is within the spirit and scope of embodiments of the present disclosure that a medication module may comprise any practical number of individual medication compartments as long as: each compartment has a suitable and operative means 85 for detecting a medication alert signal 60; each alert device 40 placed in or on the medication module must generate a medication alert signal 60 compatible with the means used to detect that signal; and, first module alert signal 70a comprises data indicating that a medication alert signal was detected from at least one medication compartment. First module alert signal 70a may additionally comprise data identifying which medicine compartment detected medication alert signal 60.

It is also noted that it is within the spirit and scope of any of the embodiments of the present disclosure to use any practical number of individual medication modules as long as the means 83 for detecting a module alert signal is adapted to support the number medication modules desired and that additional module transmitting channels are added as needed.

Figure 6:
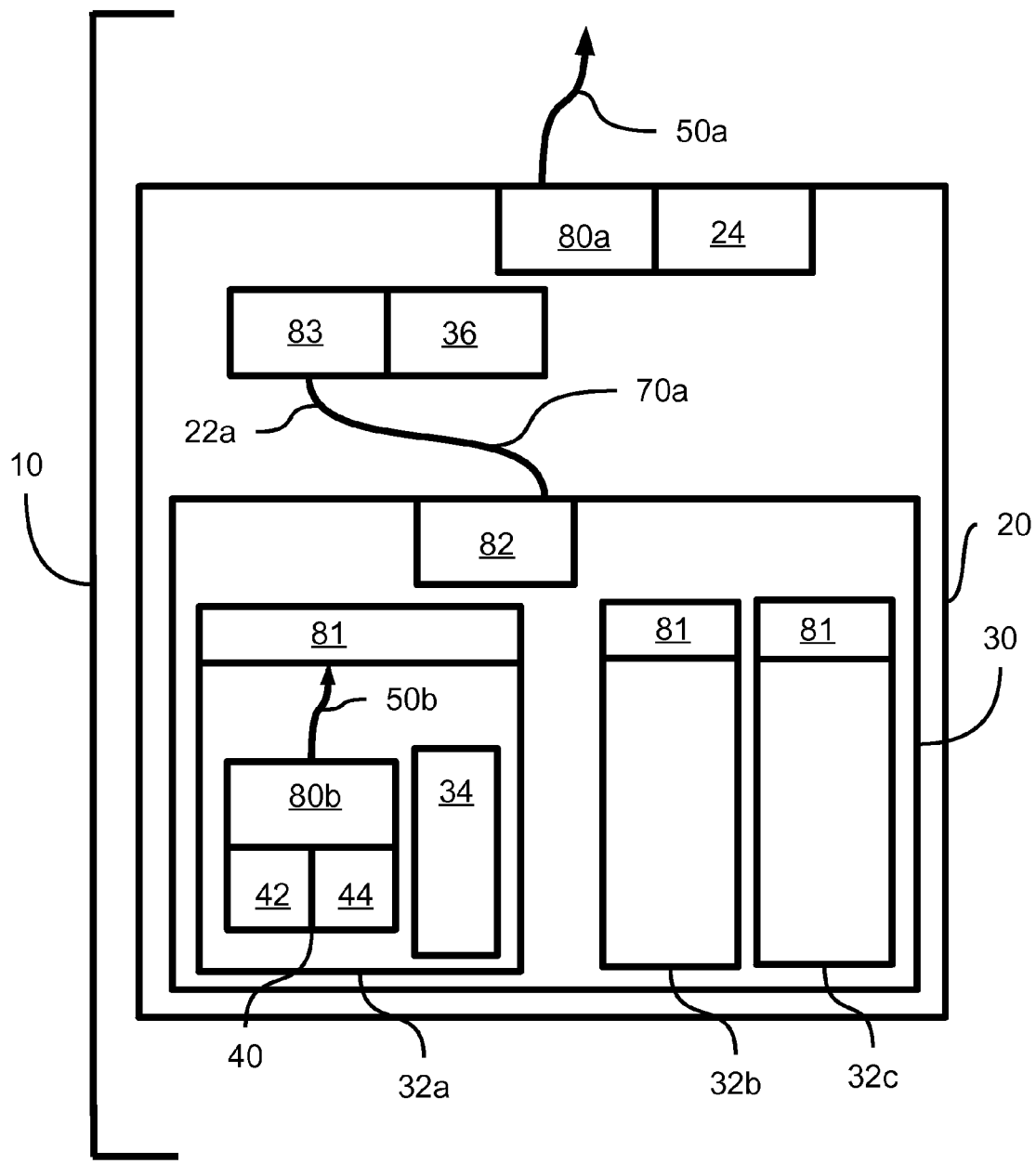
FIG. 6 shows a functional block diagram of an alert announcer system for alerting a person at medicine dosing times according to an embodiment of the present disclosure.

Turning now to FIG. 6, shown is a functional block diagram of an alert announcer system 10 for alerting a person at medicine dosing times according to an embodiment of the present disclosure. The system of FIG. 6 shows medication module 30 integrated within the primary unit 20. The plurality of medication compartments 32a, 32b, and 32c are accessible to the user and operate in the same way as the plurality of medication compartments shown in FIG. 1. The function of the components shown in FIG. 6 is the same as the function of the same components shown in FIG. 1. In addition, the operation of the system embodiment shown in FIG. 6 from the point of view of a user is the same as the operation of the system embodiment shown in FIG. 1. The system embodiment shown in FIG. 6 may be preferred in an environment where there is a single user.

Figure 7:
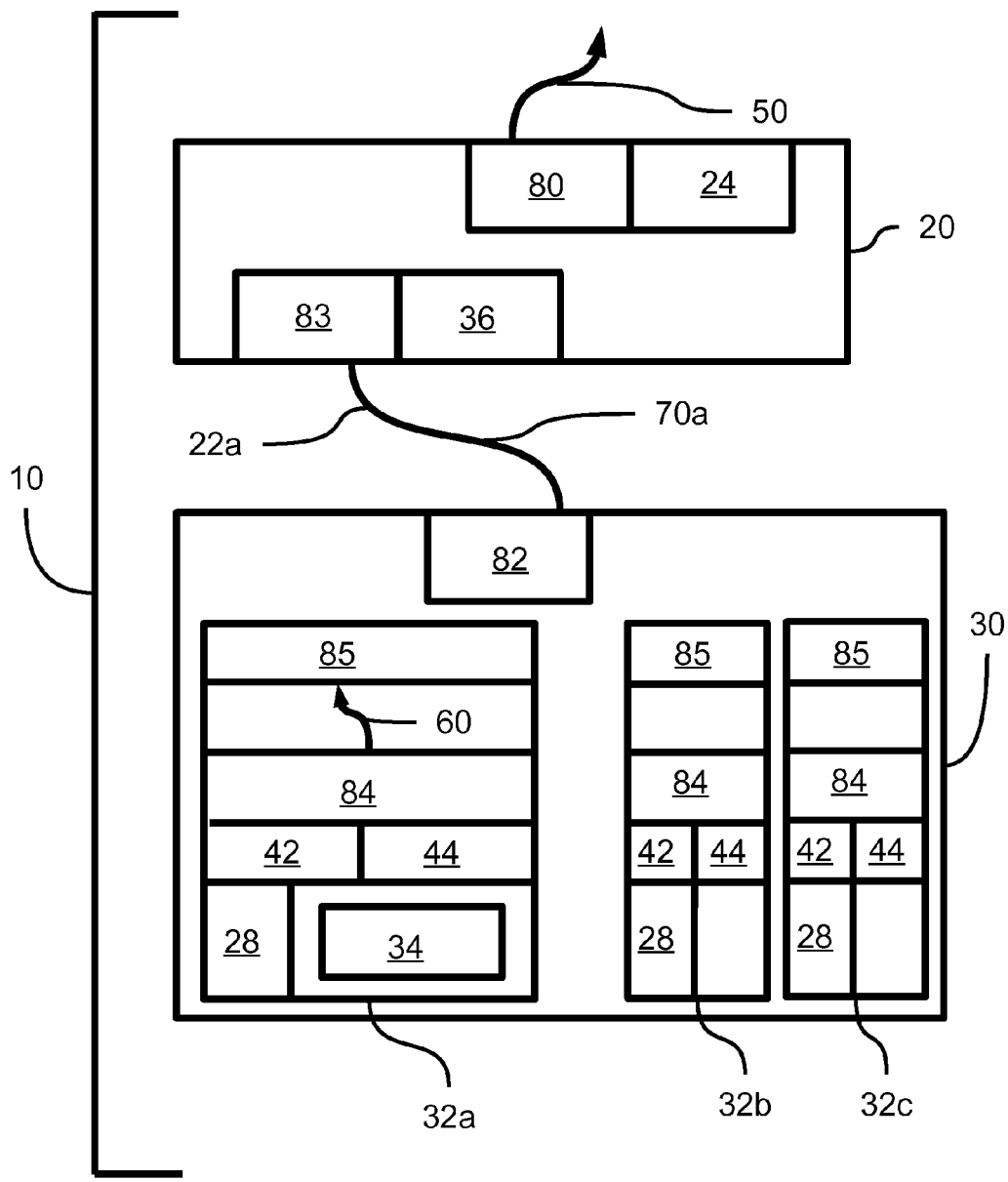
FIG. 7 shows a functional block diagram of an alert announcer system for alerting a person at medicine dosing times according to an embodiment of the present disclosure.

Turning now to FIG. 7, shown is a functional block diagram of an alert announcer system 10 for alerting a person at medicine dosing times according to an embodiment of the present disclosure. The system of FIG. 7 is shown comprising: primary unit 20 and a medication module 30. As shown in FIG. 7 primary unit 20 comprises: a means 80 for generating a sensible alert; a first module transmitting channel 22a; a means 83 for receiving a module alert signal 70a over first module transmitting channel 22a; a user responsive means 24 for selectively altering the intensity of sensible alert 50; and, a user responsive means 36 for recording, storing, and forwarding tag data. Sensible alert 50 is generated in response to receiving first module alert signal 70a. Means 36 is user responsive and operates to record, store and forward tag data associated with first module alert signal 70a. By way of example, a user may record a voice tag, perhaps the name of a person, using means 36. Means 36 may store that voice tag and then forward that voice tag to means 80 when first module alert signal 70a is detected. Means 80 may be configured to replay the recorded voice tag when sensible alert 50 is generated. The type of tag data recorded, stored and forwarded by means 36 is not limited to voice data. Tag data may include text, blinking codes, tones, music, ringtones, and other modalities that are within the capability of means 80a to produce. Means 36 may also include means to reset tag data.

In the system of FIG. 7 medication module 30 is shown further comprising: a plurality of medicine compartments 32a, 32b, and 32c; and means 82 for generating a module alert signal. Each medicine compartment comprises: a predetermined physical area suitable for the placement of a medicine container 34; means 85 for detecting a medication alert signal 60; means 84 for generating a medication alert signal which is associated uniquely with that medicine compartment wherein means 84 generates a medication alert signal 60 at medicine dosing times; electronic timing device 42 which executes a predetermined dosing schedule 44 appropriate for the medication contained in that medication compartment; and user responsive means 28 for interacting with a device executing a dosing schedule. Medication module 30 transmits first module alert signal 70a to primary unit 20 over first module transmitting channel 22a in response to detecting medication alert signal 60. Means 82 for generating module alert signal operates to generate first module alert signal 70a in response to medication module 30 detecting a medication alert signal from any of the medication compartments 32a, 32b, and 32c. First module alert signal 70a comprises data indicating that a medication alert signal 60 was detected from at least one medication compartment. First module alert signal 70a may additionally comprise data identifying which medicine compartment detected medication alert signal 60. User responsive means 28 for interacting with a device executing a dosing schedule may take the form of one or more switch means. User responsive means 28 may operate to start and stop the execution of the dosing schedule 44 associated with each medicine compartment.

The embodiment shown in FIG. 7 is different from previously described embodiments in that the system of FIG. 7 does not require the use of alert devices attached to or near medicine container 34. Instead, the system of FIG. 7 integrates into each medicine compartment the elements required to execute the dosing schedule and produce medication alerts at dosing time in accordance with the dosing schedule. It is noted that each medicine compartment 32 may contain both means 81 for detecting sensible alerts and means 85 for detecting medication alert signals, thereby enabling the detection of alerts as generated by means 80b for generating a sensible alert and by means 84 for generating a medication alert signal of alert device 40.

In preferred embodiments of the system shown in FIG. 7 each medicine compartment has a size and orientation that facilitates the physical placement of one or more medicine containers on, near, or within the physical space defined for each medicine compartment. Also each medicine compartment has printed substantially in or on it a representation of the dosing schedule 44 that may be executed by that the electronic timing device associated with that medicine compartment. For example, when the dosing schedule pertaining to medicine compartment 32a is one dose per day then medication alert signal 60 will be generated once per day and printing on or near medicine compartment 32a may say "Once a Day". Other common dosing schedules may be: "Every 24 Hours; "Twice a Day"; "Every 12 Hours"; "Three Times a Day"; "Every 8 Hours"; "Every 7 Days. It is noted, however, these dosing schedules are meant to be examples and thus do not make up an exclusive or exhaustive list of dosing schedules. Any appropriate dosing schedule may be used. Also, it must be pointed out that although FIG. 7 shows and embodiment of the system in which the medication module 30 has three medication compartments, embodiments having more or fewer medication compartments are entirely within the spirit and scope of the present disclosure.

Figure 8:
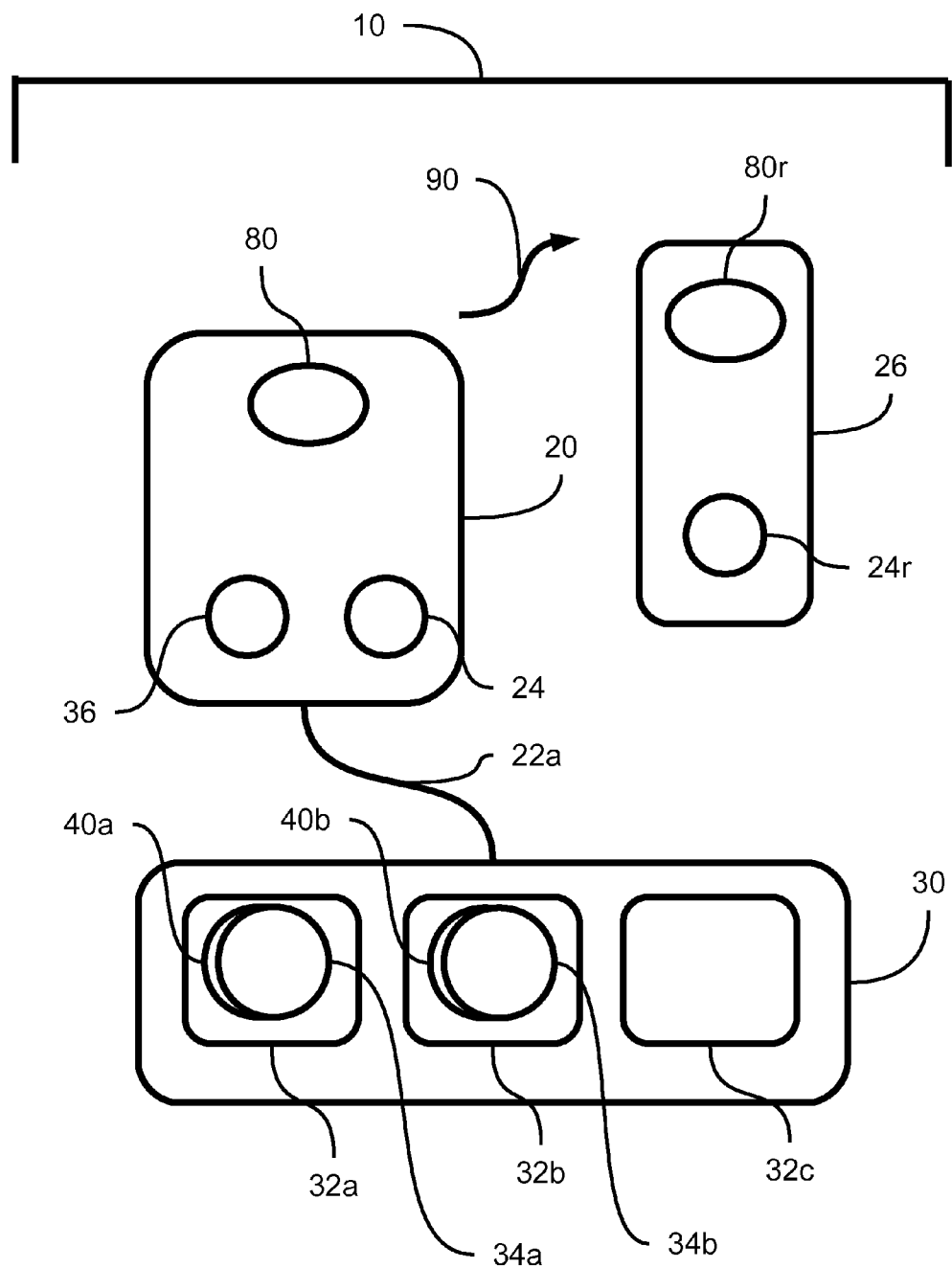
FIG. 8 shows a schematic view of an alert announcer system for alerting a person at medicine dosing times according to an embodiment of the present disclosure. The view shown in FIG. 8 is simplified to shown components of the system as they may be seen and interacted with by a user of the system.

Turning now to FIG. 8, shown is a schematic view of an alert announcer system for alerting a person at medicine dosing times according to an embodiment of the present disclosure. The view shown in FIG. 8 is simplified to shown components of the system as they may be seen and interacted with by a user of the system. Alert device 40a is shown attached to medicine container 34a and the combination is shown placed onto medicine compartment 32a. In like manner, alert device 40b is shown attached to medicine container 34b and the combination is shown placed onto medicine compartment 32b. Medicine compartments 32a, 32b, and 32c are part of medication module 30 which communicates the state of alert devices 40a and 40b to primary unit 20 using first module transmitting channel 22a. Primary unit 20 is shown comprising: means 80 for generating a sensible alert, user responsive means 24 for selectively altering the intensity of an alert; and user responsive means 36 for recording, storing, and forwarding tag data. As shown in FIG. 8 primary unit may transmit a remote alert signal 90 to remote unit 26. Remote unit 26 is shown comprising: remote means 80r for generating a sensible alert, remote user responsive means 24r for selectively altering the intensity of an alert. It is emphasized that the schematic view of the system depicted in FIG. 8 has been simplified in order to highlight the components of the system that may be visible to the user. The overall function and content of alert announcer system 10, primary unit 20, medication module 30, and remote unit 26 have been specifically described and pointed out in prior descriptions of various embodiments.

Any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of in the claims herein is not intended to invoke the provisions of 35 U.S.C. Section 112, Paragraph 6.

The invention claimed is:

1. A system, comprising:
a primary unit comprising a first module transmitting channel, the primary unit configured to:
  generate a first sensible alert,
  receive a module alert signal over the first module transmitting channel, the first sensible alert generated in response to receiving the first module alert signal.
  selectively alter an intensity of the first sensible alert, and
  record, store, and forward tag data associated with the module alert signal, wherein the tag data is forwarded when the module alert signal is received; and
a medication module comprising a plurality of medicine compartments, each of the plurality of medicine compartments comprising an alert device, each respective alert device located in proximity to or substantially within the respective medicine compartment, the respective medicine compartment configured to detect a second sensible alert emitted by the respective alert device, the medication module configured to transmit the first module alert signal to the primary unit over the first module transmitting channel in response to detecting the second sensible alert, the first module alert signal comprising data indicating that the medication module detected the second sensible alert, wherein
the alert device comprises an electronic timing device configured to execute a dosing schedule appropriate for a medicine and generate the second sensible alert, and
the second sensible alert is generated at medicine dosing times according to the dosing schedule.

2. The system of claim 1, wherein
the system additionally comprises a second medication module,
the primary unit additionally comprises a second module transmitting channel and the primary unit is configured to receive a second module alert signal over the second module transmitting channel, and
the second module alert signal comprises data identifying which medication module transmitted the second module alert.

3. The system of claim 1, wherein the first module alert signal comprises data indicating which medicine compartment detected the second sensible alert.

4. A system, comprising:
a primary unit comprising a first module transmitting channel, the primary unit configured to:

generate a first sensible alert and receive a first module alert signal over the first module transmitting channel, the first sensible alert being generated in response to receiving the first module alert signal, selectively alter an intensity of the first sensible alert, and record, store, and forward tag data associated with the module alert signal, wherein the tag data is forwarded when the module alert signal is received; and a medication module comprising a plurality of medicine compartments, each medicine compartment comprising an alert device, each respective alert device located in proximity to or substantially within the respective medicine compartment, the respective medicine compartment configured to detect a second sensible alert emitted by the respective alert device, the medication module configured to transmit the first module alert signal to the primary unit over the first module transmitting channel in response to receiving the medication alert signal, the first module alert signal comprising data indicating that the medication module detected the medicine alert signal, wherein the alert device comprises an electronic timing device configured to execute a dosing schedule appropriate for a medicine and generate the medication alert signal, and the medication alert signal is generated at medicine dosing times according to the dosing schedule.

5. The system of claim 4, further comprising a second medication module, and the primary unit additionally comprises a second module transmitting channel and is configured to receive a second module alert signal over the second module transmitting channel, the second module alert signal comprising data identifying which medication module transmitted the second module alert.

6. The system of claim 4, wherein the first module alert signal comprises data indicating which medicine compartment detected the medication alert signal.

7. A system, comprising:
a remote unit configured to:
receive a remote alert signal,
generate a remote sensible alert, the remote sensible alert generated in response to receiving the remote alert signal, and
selectively alter an intensity of the remote sensible alert;

a primary unit comprising a first module transmitting channel, the primary unit configured to:
transmit the remote alert signal,
receive a first module alert signal over the first module transmitting channel, the remote alert signal transmitted in response to receiving the first module alert signal over the first module transmitting channel,
record, store, and forward tag data associated with the module alert signal, wherein the tag data is included in the remote alert signal,
generate a sensible alert, the sensible alert generated in response to receiving the first module alert signal, and;
selectively alter an intensity of the first sensible alert; and a medication module comprising a plurality of medicine compartments, each medicine compartment comprising an alert device, each respective alert device located in proximity to or substantially within the respective medicine compartment, the respective medicine compartment configured to detect a second sensible alert emitted by the respective alert device, the medication module configured to transmit the first module alert signal to the primary unit over the first module transmitting channel in response to receiving the medication alert signal the first module alert signal comprising data indicating that the medication module detected the medication alert signal, wherein the alert device comprises an electronic timing device configured to execute a dosing schedule appropriate for a medicine and to generate the medication alert signal, and the medicine alert signal is generated at medicine dosing times according to the dosing schedule.

8. The system of claim 7, wherein the system additionally comprises a second medication module, and the primary unit additionally comprises a second module transmitting channel and is configured to receive a second module alert signal over the second module transmitting channel, the second module alert signal comprising data identifying which medication module transmitted the second module alert.

9. The system of claim 7, wherein the first module alert signal comprises data indicating which medication compartment detected the medication alert signal, and the remote alert signal comprises data indicating which medication compartment detected the medication alert signal, the remote alert signal comprising data identifying which medication module transmitted the remote alert signal.

10. A system, comprising:
a primary unit comprising a first module transmitting channel, the primary unit configured to:
generate a first sensible alert,
receive a first module alert signal over the first module transmitting channel, the first sensible alert generated in response to receiving the first module alert signal,
selectively alter an intensity of the first sensible alert, and
record, store, and forward tag data associated with the module alert signal, wherein the tag data is forwarded when the module alert signal is received; and a medication module comprising a plurality of medicine compartments, each medicine compartment comprising an electronic timing device configured to execute a dosing schedule appropriate for a medicine, each medicine compartment configured to:
generate a sensible medication alert signal, the sensible medication alert signal generated at medicine dosing times according to the dosing schedule,
detect the sensible medication alert signal, and
start and stop the execution of the dosing schedule, wherein the medication module is configured to transmit the first module alert signal to the primary unit over the first module transmitting channel in response to receiving the sensible medication alert signal, and the first module alert signal comprises data indicating that the medication module detected the sensible medication alert signal.

11. The system of claim 10, wherein the system additionally comprises a second medication module, and the primary unit additionally comprises a second module transmitting channel, for the primary unit configured to receive a second module alert signal over the second module transmitting channel, the second module alert signal comprising data identifying which medication module transmitted the second module alert.

12. The system of claim 10, wherein the first module alert signal comprises data indicating which medication compartment detected the sensible medication alert signal.

* * * * *